United States Patent [19]

Bordelon et al.

[11] 4,422,900
[45] Dec. 27, 1983

[54] SPRAY DRYING APPARATUS FOR AVAILABLE CHLORINE-CONTAINING COMPOUNDS

[75] Inventors: Kent J. Bordelon; Robert C. Eschenbacher, both of Lake Charles, La.; William H. Bridendall, Cleveland, Tenn.

[73] Assignee: Olin Corporation, New Haven, Conn.

[21] Appl. No.: 324,727

[22] Filed: Nov. 25, 1981

[51] Int. Cl.³ .......................... B01D 1/14; B01D 1/18
[52] U.S. Cl. ................................ 159/48.1; 23/293 A; 159/4 B
[58] Field of Search .............. 159/4 B, 4 D, 4 E, 4 F, 159/48.1, 4 C, 4 J, 4 R, 4 ST; 23/293 A; 239/424.5; 544/190

[56] References Cited

U.S. PATENT DOCUMENTS

| | | | |
|---|---|---|---|
| 2,085,691 | 6/1937 | Brown | 159/4 F |
| 3,004,719 | 10/1961 | Povppirt | 239/424.5 |
| 3,152,005 | 10/1964 | Tuttle | 159/48.1 |
| 3,474,849 | 10/1969 | Inchavsti | 159/4 E |
| 3,615,053 | 10/1971 | Pease et al. | 239/424.5 |
| 3,661,514 | 5/1972 | Herink | 159/48.1 |
| 3,897,007 | 7/1975 | Roy | 239/403 |
| 4,182,871 | 1/1980 | Moller | 544/190 |
| 4,244,776 | 1/1981 | Noltner et al. | 159/4 E |
| 4,374,985 | 2/1983 | Doonan et al. | 544/190 |

FOREIGN PATENT DOCUMENTS 56-844923 7/1981 Japan ................................ 239/424.5

Primary Examiner—Bradley Garris
Attorney, Agent, or Firm—Donald F. Clements; James B. Haglind

[57] ABSTRACT

Granular particles of an available chlorine-containing compound such as sodium dichloroisocyanurate are prepared by conveying a flowing stream of an aqueous slurry of the compound through a tubular chamber under pressure, injecting jets of an atomizing medium such as air into the flowing stream of said slurry to agitate and aerate said slurry, conveying the aerated slurry to an exit port in said tubular chamber, discharging the aerated slurry through said exit port into a zone of reduced pressure and enlarged area, impinging additional jets of an atomizing medium into said slurry as it passes through said exit port, whereby free expansion of said slurry into a cone of aerated droplets of said slurry is effected. The resulting droplets are contacted with a heated gas in said zone to effect evaporation of water from the aerated droplets and thereby produce dry granules of the available chlorine-containing compound.

9 Claims, 4 Drawing Figures

*Na DCCA = SODIUM DICHLOROISOCYANURATE

*Na DCCA = SODIUM DICHLOROISOCYANURATE

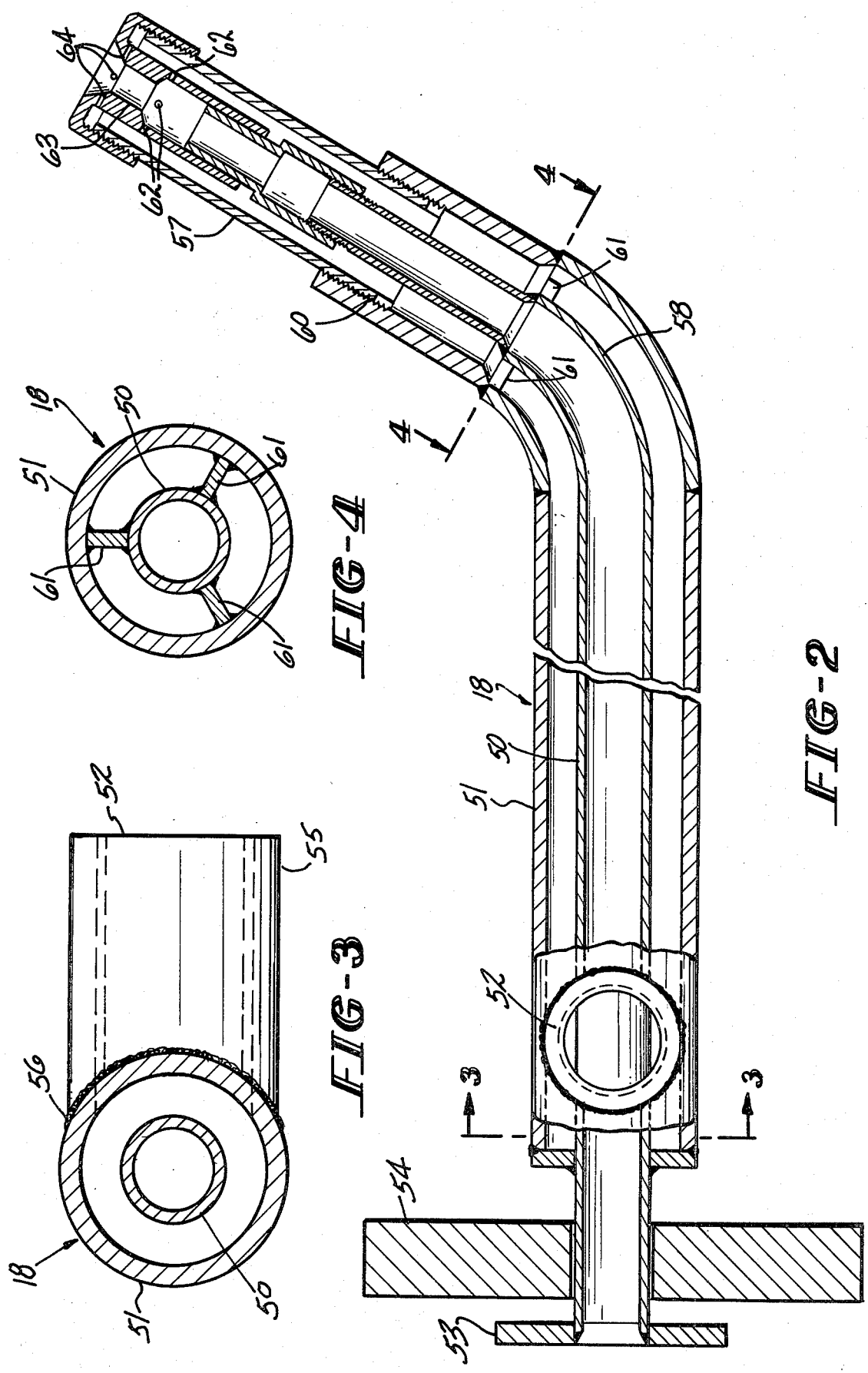

SPRAY DRYING APPARATUS FOR AVAILABLE CHLORINE-CONTAINING COMPOUNDS

This invention relates to an improved process for spray drying aqueous slurries of available chlorine-containing compounds.

The spray drying technique has been used to produce dry granular particles from aqueous slurries of a variety of solid particles. Recently efforts have been made to apply the spray drying technique to drying aqueous slurries of sodium dichloroisocyanurate, as indicated in U.S. Pat. No. 4,182,871, which issued Jan. 8, 1980, to Jens C. T. Moller. In order to to obtain a dry, granular product of desired particle size, and degree of hydration and moisture content, it is desirable to utilize a slurry with a relatively high concentration of large sodium dichloroisocyanurate crystals. Although the disclosure of this patent teaches the use of a slurry containing from about 20 to about 65 percent by weight of solids, the sole example utilizes a slurry containing 55 percent solids. When slurries of this concentration having a relatively large crystal size are conveyed to a conventional mono-fluid or two-fluid spray nozzle, it is difficult to force this highly viscous slurry of large crystals through the narrow openings of conventional mono-fluid and two-fluid spray nozzles and to achieve a high level of distribution of slurry droplets in the dryer. As a result, there is a limited contact time between the slurry droplets and the drying gases, and the capacity of the spray dryer to produce dry, granular products is seriously reduced. Because of the narrow nozzle openings utilized to effect maximum distribution of the slurry, foreign particles frequently plug the nozzle openings and plant shutdown is often required to effect nozzle cleaning. If the throughput of aqueous slurries through the nozzle is too high, caking of the slurry on the sides of the spray dryer occurs and valuable time is lost in cleaning this cake from the interior of the spray dryer.

There is need at the present time to provide an improved process for preparing dry, granular particles of available chlorine-containing compounds by the spray drying technique.

It is an object of this invention to provide an improved process for preparing granular available chlorine-containing compounds by the spray drying technique.

Another object of the invention is to provide an improved spraying technique for producing aerated droplets of aqueous slurry of available chlorine-containing compounds.

These and other objects of the invention will be apparent from the following detailed description of the invention.

It has now been discovered that the foregoing objects are accomplished by the process of this invention for preparing granular particles of an available chlorine compound which comprises:

a. conveying a flowing stream of an aqueous slurry of said compound under pressure through a tubular chamber having a longitudinal axis parallel to the direction of flow of said slurry;

b. conveying said aerated slurry to an exit port positioned in said tubular chamber;

c. discharging said aqueous slurry from said tubular chamber through said port into a zone of reduced pressure and enlarged area;

d. impinging atomizing medium into said slurry as it passes out of said exit port into said zone, whereby free expansion of said slurry into a cone of aerated droplets of said slurry is effected; and e. contacting said droplets with heated gas in said zone to evaporate water from said droplets and produce dry granules of said compound.

FIG. 2 shows a longitudinal vertical section of a preferred tubular chamber design useful in atomizing the aqueous slurry.

FIG. 3 is a sectional view along line 3—3 of FIG. 2.

FIG. 4 is a sectional view along line 4—4 of FIG. 2.

Figure 1:
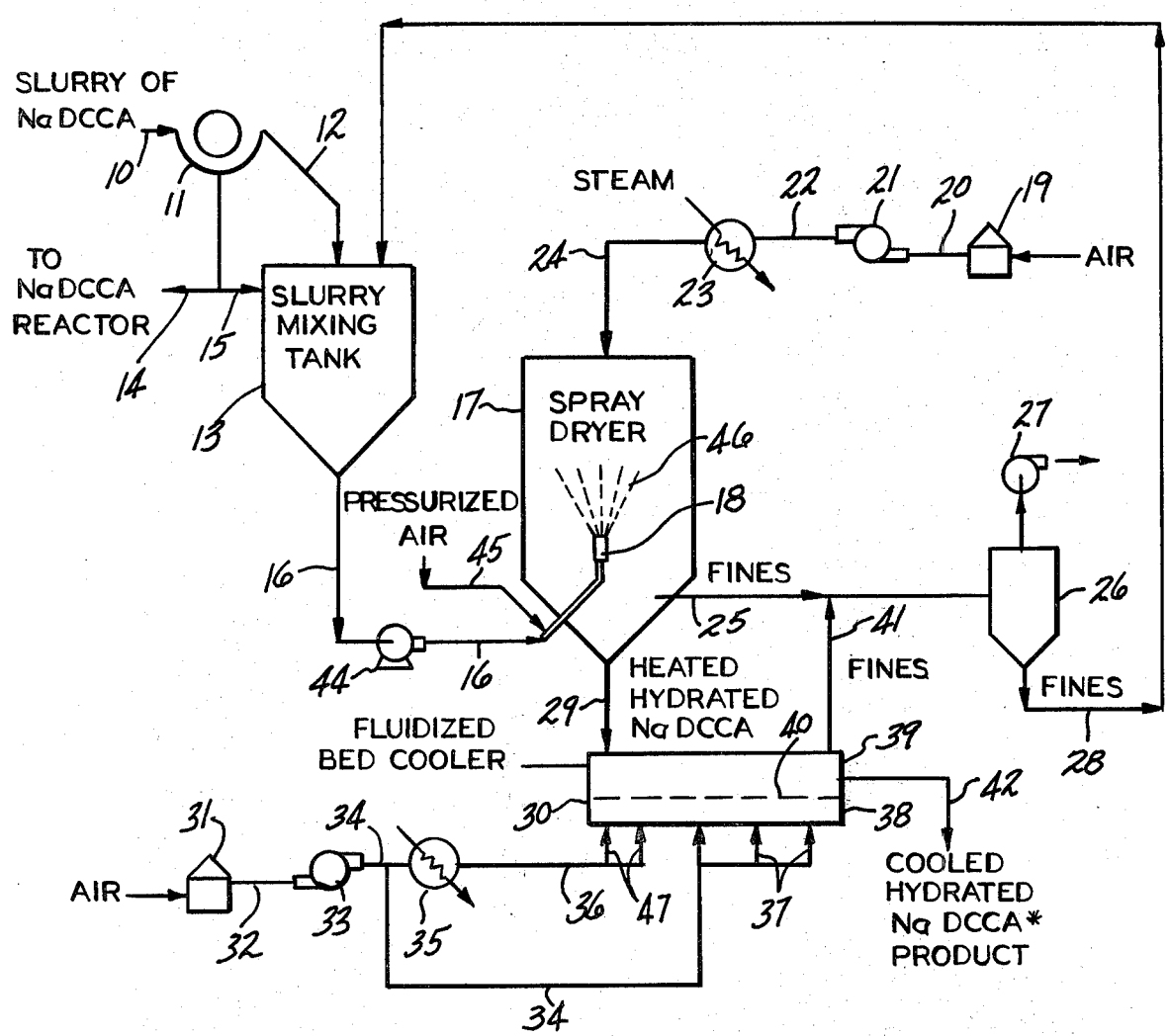
FIG. 1 shows in schematic form a perferred embodiment of the process of this invention in which an aqueous slurry of sodium dichloroisocyanurate is spray dried, and the resulting heated hydrated particles are cooled in a fluidized bed.

In more detail, referring to FIG. 1, a slurry of sodium dichloroisocyanurate is fed through slurry line 10 to filter 11, where the slurry is separated into a filter cake and a filtrate. The filter cake is conveyed through cake line 12 to slurry mixing tank 13. The filtrate is recycled through filtrate line 14 to the reactor used in the preparation of the sodium dichloroiscyanurate slurry, or otherwise disposed of. If desired, a portion of the filtrate may be conveyed through bleed line 15 to the slurry mixing tank 13 to adjust the water concentration of the slurry to the desired level.

The aqueous slurry is conveyed from slurry mixing tank 13 through spray dryer feed line 16 by means of slurry pump 44 and conveyed under pressure to spray dryer 17 through tubular chamber 18 where it is mixed with atomizing medium such as pressurized air fed through atomizing feed line 45. The slurry is aerated in tubular chamber 18 and sprayed into spray dryer 17, a zone of reduced pressure and enlarged area, where the slurry is expanded into a cone 46 of aerated droplets of said slurry.

Atmospheric air or other suitable inert gas is drawn into air filter 19 and through feed line 20 by means of blower 21. The clean air is conveyed through air line 22 to heat exchanger 23, where the temperature of the air is increased sufficiently to evaporate free water from the droplets of aqueous slurry of sodium dichloroisocyanurate. Heated air is conveyed through heated air line 24 to the top of spray dryer 17, where it passes as a moving stream of heated gas from the top of dryer 17 across the droplets in cone 46 and out of air discharge line 25.

Pressure applied by blower 21 is sufficient to convey the heated gas along this path and into cyclone 26, which separates any fine particles of sodium dichlorisocyanurate contained therein. Fines-free air is discharged from the top of cyclone 26 through discharge blower 27. Fines are collected in cyclone 26 and conveyed through fines recycle line 28 to slurry mixing tank 13.

When the moving stream of heated gas from heated air line 24 contacts the droplets of aqueous slurry of sodium dichloroisocyanurate discharged from tubular chamber 18, free water is evaporated from the droplets which dilutes and cools the heated air stream. The droplets, as a result of this drying technique, form heated porous solid spherical particles of hydrated sodium dichloroisocyanurate.

These solids fall to the bottom of spray dryer 17, where they are discharged through heated hydrated sodium dichloroisocyanurate line 29. Any fines contained in the particles are withdrawn with the cooled air stream through air discharge line 25.

The heated hydrated solids are conveyed through line 29 to the top of fluidized bed cooler 30, which is fed with cool gas such as air. The air is conveyed through air filter 31, through air feed line 32 by means of blower 33 and through air line 34 to manifold ports 37 and into the bottom portion 38 of fluidized bed cooler 30. The temperature of the hydrated particles is reduced below about 50° C. If desired a portion of the air is heated in heat exchanger 35 and conveyed through heated air line 36 to dryer manifold 47 to effect post heating of the particles in cooler 30.

Heated hydrated particles from line 29 are conveyed to the upper portion 39 of fluidized bed cooler and collect on screen 40, which separates upper portion 39 from bottom portion 38. The openings in screen 40 are sufficiently large to permit the passage of cooling gas into upper portion 39, but sufficiently small to prevent the passage of the heated hydrated particles into bottom portion 38.

The cooled air passes from manifold ports 37 through bottom portion 38, through the openings in screen 40 into the upper portion 39 where it contacts the heated hydrated particles and passes through spent air exit 41. Upon contact with the heated hydrated particles, there is a transfer of energy between the gas and solids. Motion is imparted to the particles by the gas, which lifts the particles above screen 40 and conveys them to particle exit 42. While traveling this path, a thermal transfer between the cooling gas and particles occurs at a rate sufficient to reduce the temperature of the particles to below about 50° C. In addition, a hydration equilibrium is imparted to the particles to produce dry, cooled porous solid spherical particles of hydrated sodium dichloroisocyanurate. These particles are discharged through particle exit 42, and conveyed to packaging or storage (not shown). As the cooled gas contacts the heated particles in fluidized bed cooler 30, any fines remaining in the particles are carried with the spent gas through spent air exit line 41 for further processing. The spent gas stream in 41 is combined with the contents of air discharge line 25, as shown in FIG. 1 and conveyed to cyclone 26. If desired, the spent gas and fines may be fed directly to cyclone 26 or another cyclone.

FIG. 2 is a longitudinal, vertical section of a preferred tubular chamber design 18. A flowing stream of aqueous slurry of available chlorine-containing compound such as sodium dichloroisocyanurate is conveyed from spray dryer feed line 16 (not shown) to slurry supply line 50. Pressurized air or other atomizing medium is conveyed through atomizing feed line 45 (not shown) to a larger supply line 51 which surrounds slurry supply line 50 on one side of the tubular chamber 18. Atomizing medium is fed into supply line 51 through atomizing feed port 52. Secured to the end of slurry supply line 50 is connecting plate 53 and connecting flange 54 which are used to secure slurry supply line 50 to spray dryer feed line 16.

FIG. 3 is a sectional view through lines 3—3 of FIG. 2 which shows atomizing feed port 52 and connector 55 which is utilized to connect with atomizing feed line 45. Connector 55 is secured to supply ine 51 by means of welds 56.

FIG. 2 also shows at the end of the tubular chamber 18, opposite from connecting flange 54, that there is secured a mixing nozzle 57. Tubular chamber 18 is preferably provided with a suitable bend 58 so that when tubular chamber 18 is secured to the wall of spray dryer 17, the central axis of mixing nozzle 57 is in a substantially vertical position in the center of spray dryer 17. As a result, the cone 46 of aerated droplets of aqueous slurry will be sprayed in an upwardly direction uniformly through the cross section of the spray dryer 17.

Mixing nozzle 57 is secured to the end of tubular chamber 18 by any suitable means such as threads 60.

Referring to FIG. 4, which is a cross section of tubular chamber 18 through lines 4—4 of FIG. 2, there is shown a supporting device for separating air supply line 51 from slurry supply line 50 at the opposite end of tubular chamber 18. Support members 61 are preferably welded between the interior of supply line 51 and the exterior of slurry supply line 50 in order to maintain a uniform distribution of atomizing medium on the outside of slurry supply line 50.

In mixing nozzle 57, a plurality of small holes or jet openings which comprise first apertures 62 are positioned in the wall of slurry supply line 50. These apertures are preferably positioned tangentially to the longitudinal axis of mixing nozzle 57 so that when air under pressure is forced from the chamber between supply line 51 and slurry supply line 50 into the aqueous slurry contained in slurry supply line 50, a rotary motion is imparted to the slurry within slurry supply line 50. In addition, this aqueous slurry is also aerated in view of the air which is injected into the slurry through these first apertures 62. The aerated slurry is then conveyed under pressure to exit port 63 where the resulting aerated slurry is further contacted with air under pressure through a plurality of ports or jets which comprise second apertures 64. If desired, first apertures 62 may be eliminated.

In a preferred embodiment of the invention, exit port 63 is of a reduced cross sectional area to provide a nozzle effect upon the aerated slurry as it passes out of the mixing nozzle 57. In addition, first apertures 62 and second apertures 64 are preferably positioned tangentially to the longitudinal axis of mixing nozzle 57 in order to impart the rotating motion to the aqueous slurry as it travels through mixing nozzle 57. This rotating motion not only increases the agitation of the aqueous slurry, but also enhances the aeration of the aqueous slurry by the air which is injected under pressure through first apertures 62 and second apertures 64.

As shown in FIG. 1, the aerated, agitated slurry discharged from tubular chamber 18 is fed into a zone of reduced pressure and enlarged area which permits free expansion of the aqueous slurry into a cone of aerated droplets. These are subsquently dried in the spray dryer to form dry, granular products of sodium dichloroisocyanurate dihydrate.

One skilled in the art will recognize that although the process of the invention has been described with respect to sodium dichloroisocyanurate, it can be also utilized in the preparation of anhydrous sodium dichloroisocyanurate as well as trichloroisocyanuric acid, calcium hypochlorite, and the like. For purposes of simplicity, however, the invention has been described with respect to a typical product, sodium dichloroisocyanurate hydrate.

Any suitable atomizing medium may be employed that is inert to the sodium dichloroisocyanurate. Air, nitrogen, carbon dioxide and the like may be employed, but air is preferably used.

In carrying out the process of this invention, it is preferred to provide from about 50 to about 100% of the total air fed to tubular chamber 18 through the second apertures 64 located in exit port 63 and the remainder of the atomizing air is fed through the first apertures 62. The pressure of the aqueous slurry fed to slurry supply line 50 is generally in the range from about 30 to 40 and preferably in the range from about 32 to about 37 psig. The pressure of the atomizing medium, such as air fed to supply line 51 is generally in the range of from about 50 to about 60 and preferably from about 52 to about 57 psig.

In order to minimize buildup of wet solids on the walls of the spray dryer and produce a product having the desired degree of dryness, and particle size distribution, the air flow ratio is maintained in the range between about 0.1 and about 0.25, and preferably between about 0.12 and about 0.20. The "air flow ratio" is defined as:

$$\frac{\text{LBS air}}{\text{LB slurry}} = \frac{\text{air SCFM} \times 0.076 \text{ LB/SCFM air}}{\text{GPM slurry} \times 8.34 \text{ LB H}_2\text{O/LB slurry} \times \text{specific gravity}}$$

A suitable mixing nozzle of the type useful in the process of this invention is described in U.S. Pat. No. 3,897,007 which issued July 29, 1975, to Joseph G. Roy. This patent is hereby incorporated in its entirety by reference. As pointed out in that patent, the two fluid mixing nozzle of this type utilizes a relatively large opening in the slurry supply line 50 and in the exit port 63.

Depending on the feed rate, these openings may be as large as desired. Typically the nozzle opening is in the range from about $\frac{1}{8}''$ to about $\frac{1}{2}''$ and preferably from about $\frac{1}{4}''$ to about $\frac{3}{8}''$ in diameter and still provide the desired degree of dispersion of aerated slurry for satisfactory drying in the spray dryer. As a result of these large openings there is virtually no plugging of the spray nozzle during operation of the process. In contrast, when conventional single or two fluid nozzles are utilized, relatively small ports, such as in the range from about 1 to about 3 millimeters in diameter, must be used in order to effect the desired degree of dispersion of the aerated slurry. In view of the small size of the prior art nozzle openings, any foreign matter or large crystals in the aqueous slurry fed to the nozzle will immediately plug the nozzle and cause an extended shutdown of the process in order to clean the nozzle. The novel process of this invention substantially minimizes the downtime of the process due to nozzle plugging.

In carrying out the process of this invention, an aqueous slurry of sodium dichloroisocyanurate is prepared by any convenient technique. For example, U.S. Pat. Nos. 3,035,056 and 3,035,057, which issued on May 15, 1962, to William F. Symes and William F. Symes et al., respectively, describe the preparation of sodium dichloroisocyanurate from chlorine and trisodium isocyanurate. However, any convenient technique for preparing aqueous slurries of sodium dichloroisocyanurate may be employed. Generally slurries produced by these techniques have a solid content below about 40% by weight.

In addition, the process described in U.S. Pat. No. 4,182,871 which issued Jan. 8, 1980, to Jens C. T. Moller for the preparation of sodium dichloroisocyanurate may also be substantially improved by applying the improved process of this invention.

In order to prepare a suitable slurry feed for spray dryer 17, any pumpable, sprayable slurry containing greater than about 40% weight of sodium dichloroisocyanurate is employed. The concentration of sodium dichloroisocyanurate is preferably increased to a range from about 50 to about 60 percent, by filtration, centrifuging, or any other suitable technique.

The sodium dichloroisocyanurate slurry may be sprayed from nozzles in any position in any suitable direction in the dryer, which as the upper part or the lower part, or in downwardly, upwardly or transverse direction. In a preferred embodiment, the nozzles are located in the center of the lower part of the dryer and the slurry sprayed upward in the manner of a fountain, as illustrated in FIG. 1.

After the slurry has left the nozzles as droplets and the droplets are contacted with the moving bed of heated gas, water is evaporated and porous solid spherical particles of the sodium dichloroisocyanurate hydrate are formed. The heated gas is any inert gas such as air, nitrogen, carbon dioxide, or the like. The temperature of the heated gas fed through heated air line 24 is generally in the range from about 170° to about 250° C. and preferably in the range from about 185° to about 220° C. The particles are dried to a spherical form having the desired degree of hydration by controlling the temperature of the moisture-bearing gas leaving the spray dryer. The outlet temperature of this gas is maintained, for example, in the range of from about 100° to about 150° C., and preferably from about 100° to about 110° C. by controlling the gas inlet temperature. The heated particles having free water removed are discharged from the spray dryer after an average residence time of from about 10 to about 60 seconds and preferably from about 15 to about 30 seconds of elapsed time from the time when the slurry is sprayed until the time when the solid, dried particles are removed from the dryer.

The heated sodium dichloroisocyanurate hydrate particles removed from spray dryer 17 are fed to the upper portion 39 of fluidized bed cooler 30 at a temperature in the range from about 50° to about 100° C., and preferably from about 70° to about 80° C.

Any suitable fluid bed cooler may be used for cooling the heated particles. A preferred fluid bed cooler is one having a vibrating means for agitating and conveying the particles. As the heated particles are fed to upper portion 39, they are contacted with cooling gas which passes through opening in screen 40. The cooling gas is any suitable inert fluidizing gas such as air, nitrogen, or carbon dioxide. The cooling gas is fed at a temperature lower than the feed temperature of the dried particles. To obtain the desired degree of cooling, gas temperatures in the range from about 15° C. to about 50° C. are quite satisfactory when gas velocities of from about 0.1 to about 0.6, preferably from about 0.2 to about 0.5, and more preferably from about 0.3 to about 0.4 meters per second are used. At these gas velocities, sufficient contact to effect the desired degree of cooling is obtained without blowing an excessive amount of solids out of spent air exit 41.

In another embodiment of the invention, two zones of cooling are employed in fluidized bed cooler 30. In the first zone, which comprises from about $\frac{1}{3}$ to about $\frac{1}{2}$ of the bed area, conditioned air at a temperature in the range from about 30 to about 100 and preferably from about 40° to about 50° C. is fed through manifold ports 37 at the feed end of fluidized bed cooler 30. In the second zone, which comprises from about $\frac{1}{2}$ to about $\frac{2}{3}$ of the bed area, conditioned air at a temperature in the range from about 20 to about 40 and preferably from about 25° to about 35° C. is fed through manifold ports 37 at the discharge end of fluidized bed cooler 30.

To produce a cool, dry product having the desired amounts of water of hydration in either cooling embodiment, the relative humidity of the fluidizing cooling gas is controlled at a relatively constant level. While it will be recognized that by employing dry, fluidizing gases, some drying may be carried out in the fluid bed cooler. This is minimized by employing fluidizing cooling gases having a relative humidity of from about 25 to about 50, and preferably from about 30 to about 40 percent.

The fluidized bed cooler 30 is operated to provide a retention time of the solids in the fluidized bed of from about 2 to about 20, and preferably from about 5 to about 15 minutes. Free-flowing sodium dichloroisocyanurate hydrate particles having a temperature below about 50° C., and preferably in the range of about 30° to about 40° C., are removed from the fluidized bed cooler 30. These solids are porous said spherical, dust-free particles of hydrated sodium dichloroisocyanurate which have a uniform distribution of water of hydration therein.

Particles of sodium dichloroisocyanurate hydrates having any desired water content may be produced by the process of the present invention, for example, those having a water of hydration content of from about 7 to about 14 percent by weight. In a preferred embodiment, sodium dichloroisocyanurate hydrate having a water content in the range of from about 12 to about 13.5 is produced.

Particle size of the cooled, dry hydrated product of this invention is in the range of from about 100 to about 420 microns and preferably from about 150 to about 330 microns in diameter. Control of the particle size is effected by proper adjustment of the air to slurry ratio.

Bulk densities of products produced by the process of this invention are in the range of from about 30 to about 50, and preferably from about 38 to about 45 pounds per cubic foot. Particle bulk densities are determined by the American Standard for Testing Materials Method B527-70, Standard Test Method for Tap Density of Powders of Refractory Metals and Compounds by Tap-PAK Volumeter.

The novel spherical, porous particles of alkali metal isocyanurate produced by the novel process of the present invention are free-flowing, have no sharp edges, are dust-free, are readily soluble in liquids such as water, have a favorable bulk density and contain substantially uniform amounts of water of hydration.

To further illustrate the process of the present invention, the following EXAMPLE is presented. All percentages are by weight unless otherwise specified.

EXAMPLE

A spray dryer constructed of titanium having a diameter of about 6 meters and a height of about 12.8 meters from the bottom of the cone to the dryer top was utilized to prepare dry, granular sodium dichloroisocyanurate hydrate in accordance with the process of this invention. The spray dryer was provided with a 2-fluid nozzle of the type shown in FIG. 2 utilizing air to aerate the aqueous slurry of sodium dichloroisocyanurate. Hot air was forced into the top of the spray dryer and dry, granular product was removed from the bottom of the cone at the bottom thereof. An exit port was provided in the side of the spray dryer to remove cooled, drying air and any fines that were produced during the drying operation.

An aqueous slurry of sodium dichloroisocyanurate containing about 52 percent by weight was fed to the 2-fluid nozzle at the rate of about 4 gallons per minute and at a pressure of about 35 psig. Pressurized air was fed to the 2-fluid nozzle at the rate of about 90 SCFM and at a pressure of about 55 psig. The weight ratio of air to slurry was 0.15.

The mixing nozzle portion of the tubular chamber 18 contained 4 ports in the first aperture series which were tangential to the longitudinal axis of mixing nozzle 57. These ports had a diameter of approximately 2 millimeters. The diameter area of the slurry supply line 50 adjacent to the entrance of the first apertures was approximately 9 millimeters. The exit port 63 had a length of approximately 10 millimeters and a cross sectional diameter of approximately 8 millimeters. Four additional ports utilized for injecting air into the aerated spray as it exited from the mixing nozzle 57 each had a diameter of approximately 2 millimeters.

The pressure in the spray dryer was maintained at about minus one-half inch column of water.

The temperature of the drying air as it entered the spray dryer was approximately 200° C. and the temperature of the exit air containing fines removed through air discharge line 25 was approximately 105° C.

The hot product was fed to a fluidized bed cooler (Niro Atomizer, Inc. Vibro-fluidizer) having a vibrating bed. The cooler was fed with air at 25° C. and a relative humidity of 40 percent with a velocity in the bed of 0.35 m./sec. The product had a final temperature of 35° C., a moisture content of 12 percent and consisted of porous spheres having the following particle size:

| U.S. Standard Screen, Mesh | % Retained |
| --- | --- |
| 40 | 7.9 |
| 70 | 55.1 |
| 100 | 24.3 |
| 200 | 12.3 |
| Pan | 0.4 |

During the cooling stage, product retention time in the fluid bed cooler was an average of about 10 minutes. The product recovered had a bulk density of about 38 pounds per cubic foot, an available chlorine content of about 56 percent. Analysis of screen fractions of the hydrated product showed the moisture content to be evenly distributed among the various screen fractions. The cooled product was found to be dust-free and free-flowing with no evidence of caking.

Extended operation of the spray dryer utilizing the novel tubular chamber 18 of this invention permitted operation of the process for over 120 days without any plugging of the mixing nozzle portion 57 of tubular chamber 18.

For purposes of comparison, the process was repeated using a single fluid nozzle having a opening of approximately one millimeter in diameter. Operation of the dryer with the single fluid nozzle resulted in plugging of the nozzle after operation of the spray dryer after a period of only 4 hours.

What is claimed is:

1. A process for preparing granular particles of an available chlorine compound which comprises:

a. conveying a flowing stream of an aqueous slurry of said compound under pressure through a tubular chamber having a longitudinal axis parallel to the direction of flow of said slurry;
b. conveying said slurry to an exit port positioned in said tubular chamber;
c. discharging said aqueous slurry from said tubular chamber through said port into a zone of reduced pressure and enlarged area;
d. conveying jets of atomizing medium into said exit port, thereby impinging said jets of atomizing medium into said slurry as it passes out of said exit port into said zone, whereby free expansion of said slurry into a cone of aerated droplets of said slurry is effected, and
e. contacting said droplets with heated gas in said zone to evaporate water from said droplets and produce dry granules of said compound.

2. The process of claim 1 wherein additional atomizing medium is injected tangentially into said flowing stream under pressure before said slurry reaches the confines of said exit port, whereby additional agitation and aeration of said slurry is effected.

3. The process of claim 2 wherein the proportion of atomizing medium injected into said exit port ranges from about 50 to about 100 percent of the total atomizing medium injected into said slurry in said tubular chamber.

4. The process of claim 3 wherein said atomizing medium is injected as jets under pressure at a plurality of points within said tubular chamber.

5. The process of claim 4 wherein said atomizing medium is air.

6. The process of claim 1, 2, 3, 4 or 5 wherein the injection of said atomizing medium is tangential to said longitudinal axis, thereby imparting a rotary motion to said slurry as it moves along said axis.

7. The process of claim 1, 2, 3, 4 or 5 wherein said available chlorine compound is sodium dichloroisocyanurate.

8. The process of claim 1, 2, 3, 4 or 5 wherein said available chlorine compound is trichloroisocyanurate.

9. The process of claim 1, 2, 3, 4 or 5 wherein said available chlorine-containing compound is calcium hypochlorite.

* * * * *